(12) United States Patent
White et al.

(10) Patent No.: US 10,639,259 B2
(45) Date of Patent: May 5, 2020

(54) WATER-BASED COSMETIC COMPOSITIONS

(71) Applicant: L'ORÉAL, Paris (FR)

(72) Inventors: Geoffrey White, Old Bridge, NJ (US); Brian Scott Bodnar, Manasquan, NJ (US)

(73) Assignee: L'ORÉAL, Paris (FR)

( * ) Notice: Subject to any disclaimer, the term of this patent is extended or adjusted under 35 U.S.C. 154(b) by 730 days.

(21) Appl. No.: 14/925,125

(22) Filed: Oct. 28, 2015

(65) Prior Publication Data
US 2017/0119644 A1    May 4, 2017

(51) Int. Cl.
| | | |
|---|---|---|
| *A61K 8/49* | (2006.01) | |
| *A61K 8/39* | (2006.01) | |
| *A61K 8/81* | (2006.01) | |
| *A61Q 17/04* | (2006.01) | |
| *A61K 8/06* | (2006.01) | |
| *A61K 8/894* | (2006.01) | |

(52) U.S. Cl.
CPC ............ *A61K 8/4946* (2013.01); *A61K 8/062* (2013.01); *A61K 8/39* (2013.01); *A61K 8/4973* (2013.01); *A61K 8/4993* (2013.01); *A61K 8/8152* (2013.01); *A61K 8/894* (2013.01); *A61Q 17/04* (2013.01)

(58) Field of Classification Search
None
See application file for complete search history.

(56) References Cited

U.S. PATENT DOCUMENTS

2010/0278763 A1* 11/2010 Loeffler ............... A61K 8/8158
424/59
2014/0202485 A1* 7/2014 Wang .................... A61K 8/731
132/206

OTHER PUBLICATIONS

ACULYN™ 22 Rheology Modifier/Stabilizer a Very Efficient Thickener for Difficult to Thicken Surfactant Systems, Rohm and Haas, 2006, 12 pp.

* cited by examiner

*Primary Examiner* — Jeffrey T. Palenik
(74) *Attorney, Agent, or Firm* — Oblon, McClelland, Maier & Neustadt, L.L.P.

(57) ABSTRACT

Compositions containing (1) water, (2) at least one hydrophilic sunscreen active agent having a sulfonic acid group, (3) at least one surfactant selected from the group consisting of alkoxylated fatty alcohols, sorbitan esters, alkoxylated silicones, and mixtures thereof, and (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol are provided.

19 Claims, No Drawings

WATER-BASED COSMETIC COMPOSITIONS

FIELD OF THE INVENTION

The present invention relates to cosmetic compositions comprising (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, and (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol.

BACKGROUND OF THE INVENTION

"Oil-free" compositions are preferred for certain applications in the cosmetics industry because of their water content. However, such water-based cosmetic compositions are often tacky when they include an acrylate-based thickener. Further, such cosmetic compositions have a tendency to pill on application when they contain acrylate-based thickeners. Thus, despite perceived benefits from water content, such water-based compositions can be problematic when acrylate-based thickeners are used, resulting in unstable, tacky and/or pilling compositions.

Thus, there remains a need for improved cosmetic compositions which have acceptable or improved stability, feel (reduced tackiness) and/or spreadability (reduced pilling) for application to keratin materials such as skin or lips.

Accordingly, one aspect of the present invention is to provide a care and/or makeup and/or treatment composition for keratinous material such as the skin or lips, which is able to address or overcome at least one of the aforementioned problems with the prior art compositions, as well as to provide methods for using and making such compositions.

SUMMARY OF THE INVENTION

The present invention relates to cosmetic compositions comprising (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, and (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol.

The present invention relates to color cosmetic compositions comprising (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol, and (5) at least one coloring agent.

The present invention also relates to methods of treating, caring for and/or making up keratinous material (for example, skin or lips) by applying compositions of the present invention to the keratinous material in an amount sufficient to treat, care for and/or make up the keratinous material.

The present invention further relates to covering or hiding skin defects associated with keratinous material (for example, skin or lips) by applying compositions of the present invention to the keratinous material in an amount sufficient to cover or hide such skin defects.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, improved stability, reduced tackiness and/or reduced pilling on application, wherein the compositions comprise (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, and (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol, and optionally at least one coloring agent.

The present invention also relates to methods of making a composition comprising combining (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, and (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol, and optionally at least one coloring agent, and forming a cosmetic composition.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about."

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Physiologically acceptable medium" is means a medium that is compatible with human keratin materials, for instance the skin, the lips, the nails, the eyelashes, the eyebrows or the hair.

"Cosmetic composition" means a composition that is compatible with keratin materials.

"Keratin materials" means the skin (body, face, contour of the eyes, scalp), head hair, eyelashes, eyebrows, bodily hairs, nails and/or lips.

"Film former" or "film forming agent" as used herein means a polymer that, after dissolution in at least one solvent, leaves a film on the substrate to which it is applied, for example, once the at least one solvent evaporates, absorbs and/or dissipates on the substrate.

"Waterproof" as used herein refers to the ability to repel water and permanence with respect to water. Waterproof properties may be evaluated by any method known in the art for evaluating such properties. For example, a composition may be applied to skin, and the skin may be submerged in water for a certain amount of time. The amount of composition remaining on the skin after the pre-ascertained amount of time may then be evaluated and compared.

"Transfer resistance" as used herein refers to the quality exhibited by compositions that are not readily removed by contact with another material, such as, for example, a glass, food, a kimwipe, an item of clothing or the skin, for example, when eating, drinking or wiping. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred or substrate (e.g., bioskin) from a wearer to any other substrate, such as transfer from the neck of an individual to a collar or transfer from bioskin to a kimwipe after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. "Transfer resistance" could also be determined via in-vitro methods using bioskin as known by those of ordinary skill in the art. For example, whether or not a composition is transfer-resistant could be determined by whether a composition does not transfer when applied onto a bioskin substrate and wiped with a kimwipe. In a preferred embodiment of the present invention, little or no composition is transferred to the substrate. Thus, transfer-resistant compositions include transfer-free compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (or lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Make-up composition" as used herein means any composition applied to keratin materials for aesthetic purposes. Examples of acceptable make-up compositions include, but are not limited to, lip compositions such as lipsticks, foundations, eye shadows and mascaras.

The compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratin materials.

The compositions of the present invention may be in any form. They may be an emulsion, such as an oil-in-water or water-in-oil emulsion, a multiple emulsion, such as an oil-in-water-in-oil emulsion or a water-in-oil-in-water emulsion, or a solid gel, including anhydrous gels. The compositions of the invention may, for example, comprise an external or internal fatty phase. The compositions of the invention may be transparent or clear. The compositions can also be a molded composition or cast as a stick or a dish. The compositions can be a solid such as a molded stick or a poured stick. The compositions may also be liquid.

According to preferred embodiments, the compositions of the present invention lack effective amounts of oil (that is, contain 3% or less of oil, preferably contain 2% or less of oil, and preferably contain 1% or less of oil). For purposes of determining the amount of oil present in the compositions according to these embodiments, the amount of sunscreen active agent should not be considered.

According to preferred embodiments, the compositions of the present invention are solid, where the solid nature of the compositions can be determined by determining the hardness of the compositions. The hardness of a composition may, for example, be expressed in gramforce (gf). The inventive compositions of the present invention have a hardness of at least 40 gf, typically from about 40 gf to about 300 gf, most typically from about 40 gf to about 175 gf.

The hardness of the compositions can be assessed using the "cheese wire" method. This method involves cutting an 8.1 mm diameter stick composition (also known as a "slim bullet") or a 12.7 mm in diameter stick composition (also known as a "chubby bullet") and measuring its hardness at 20° C. using a tensile testing machine (dynamometer) from Chatillon Ametek at a speed of 100 mm/minute. The hardness value from this method is expressed in grams as the shear force required to cut a stick under the above conditions. According to this method, the hardness of compositions according to the present invention which may be in stick form may, for example, range from about 40 gf to about 250 gf, more typically from about 40 gf to about 100 gf, most typically from about 40 gf to about 70 gf, for a sample of 8.1 mm diameter stick, and further such as from about 75 gf to about 300 gf, more typically from about 75 gf to 175 gf for a sample of 12.7 mm diameter stick.

Unless otherwise indicated, hardness values provided herein are for an 8.1 mm diameter stick ("slim" stick).

The hardness of the composition of the present invention preferably is such that the compositions are self-supporting and can easily disintegrate to form a satisfactory deposit on keratin substances such as the lips. In addition, this hardness imparts good impact strength to the inventive compositions, which may be molded or cast, for example, in stick or dish form.

According to preferred embodiments, the compositions of the present invention are liquid. For purposes of the present invention, a "liquid" compostion is not a solid composition as defined above, and includes composition forms commonly found in the cosmetics field such as creams and lotions. For example, liquid compositions of the present invention preferably have a viscosity ranging from 750 cps to 20,000 cps, preferably from 900 to 16,600 cps, and preferably from 1,000 to 15,000 cps, including all ranges and subranges therebetween.

Water

According to the present invention, compositions comprising water are provided. Preferably, water is present in an amount of from about 5% to about 90% by weight, preferably from about 10% to about 80% by weight, and preferably from about 20% to about 75% by weight, including all ranges and subranges therebetween (such as, for example, 25% to 75% and 10% to 90% by weight), all weights being based on the total weight of the composition.

Copolymer

According to the present invention, compositions comprising at least one copolymer comprising at least one monomer comprising a carboxylic acid containing α,β-unsaturation, at least one monomer containing an ester of a carboxylic acid containing α,β-unsaturation, and at least one monomer containing an oxyalkylenated fatty alcohol are provided.

According to preferred embodiments, the oxyalkylenated portion of the copolymer preferably comprises less than 8 carbon atoms, preferably less than 5 carbon atoms, preferably between 2 and 4 carbon atoms, with oxyethylenation (2 carbon atoms) and oxypropylenation (3 carbon atoms) being most preferred. The amount of oxyalkylenation preferably ranges from 1 to 100, preferably from 2 to 50, preferably from 2 to 30, and preferably from 2 to 21, including all ranges and subranges therebetween.

According to preferred embodiments, the fatty alcohol portion of the copolymer contains greater than 8 carbon atoms, preferably 8-50 carbon atoms, preferably 8-40 carbon atoms, preferably 8-30 carbon atoms, preferably 8-20 carbon atoms and preferably 8-16 carbon atoms, including all ranges and subranges therebetween. The fatty alcohol portion is preferably hydrogenated (for example, stearyl, lauryl, cetyl, cetearyl); however, the fatty alcohol may contain one or more double bonds (for example, oleyl).

As an example, steareth-20 is an acceptable fatty alcohol containing 16 carbon atoms and oxyethylenation of 20.

According to preferred embodiments, the copolymers comprising at least one monomer comprising a carboxylic acid containing α,β-unsaturation, at least one monomer containing an ester of a carboxylic acid containing α,β-unsaturation, and at least one monomer containing an oxyalkylenated fatty alcohol also comprise as a monomer an ester of an α,β-monoethylenically unsaturated carboxylic acid and of an alcohol having less than 8 carbon atoms, preferably an alcohol having 1-4 carbon atoms.

As an example, Aculyn 22 sold by the company Rohm & Haas, which is a methacrylic acid/ethyl acrylate/oxyalkylenated stearyl methacrylate terpolymer (also known as Acrylates/Steareth-20 Methacrylate Copolymer) is acceptable.

Preferably, the copolymer(s) comprising at least one monomer comprising a carboxylic acid containing α,β-unsaturation, at least one monomer containing an ester of a carboxylic acid containing α,β-unsaturation, and at least one monomer containing an oxyalkylenated fatty alcohol is/are in the compositions of the present invention in an amount ranging from about 2.5% to about 30% by weight based on total weight of the composition, preferably about 3% to about 25% by weight based on the total weight of the composition, and preferably about 4% to about 20% by weight based on the total weight of the composition, including all ranges and subranges therebetween.

Surfactant

According to the present invention, compositions comprising at least one surfactant selected from the group consisting of alkoxylated fatty alcohols, sorbitan esters, alkoxylated silicones, and mixtures thereof are provided.

According to preferred embodiments, compositions comprising at least one sorbitan ester are provided. The sorbitan ester can have one or more ester groups so that the ester is, for example, a mono-ester, di-ester, tri-ester, etc. Preferably, each ester portion of the surfactant contains 1-40 carbon atoms, preferably 2-30 carbon atoms, preferably 3-25 carbon atoms, and preferably 3-20 carbon atoms, including all ranges and subranges therebetween.

According to preferred embodiments, the sorbitan ester can have one or more oxyalkylenation groups. If present, each oxyalkylenation group preferably comprises less than 8 carbon atoms, preferably less than 5 carbon atoms, preferably between 2 and 4 carbon atoms, with oxyethylenation (2 carbon atoms) and oxypropylenation (3 carbon atoms) being most preferred. The amount of oxyalkylenation preferably ranges from 1 to 100, preferably from 2 to 50, preferably from 2 to 30, and preferably from 2 to 20, including all ranges and subranges therebetween.

As examples of sorbitan esters, sorbitan sesquiolate is an example of a nonoxyalkylenated compound, and polysorbate-85 is an example of an oxyalkylenated compound.

According to preferred embodiments, compositions comprising at least one alkoxylated fatty alcohol are provided. According to preferred embodiments, the alkoxylated portion of the alkoxylated fatty alcohol preferably comprises less than 8 carbon atoms, preferably less than 5 carbon atoms, preferably between 2 and 4 carbon atoms, with ethoxylation (2 carbon atoms) and propoxylation (3 carbon atoms) being most preferred. The amount of alkoxylation preferably ranges from 1 to 100, preferably from 2 to 50, preferably from 2 to 30, and preferably from 2 to 21, including all ranges and subranges therebetween.

According to preferred embodiments, the fatty alcohol portion of the alkoxylated fatty alcohol contains greater than 8 carbon atoms, preferably 8-50 carbon atoms, preferably 8-40 carbon atoms, preferably 8-30 carbon atoms, preferably 8-20 carbon atoms and preferably 8-16 carbon atoms, including all ranges and subranges therebetween. The fatty alcohol portion is preferably hydrogenated (for example, stearyl, lauryl, cetyl, cetearyl); however, the fatty alcohol may contain one or more double bonds (for example, oleyl).

As examples of alkoxylated fatty alcohols, steareth (for example, steareth-2 and steareth-21), laureth (for example, laureth-4), ceteth and ceteareth surfactants are mentioned.

According to preferred embodiments, compositions comprising at least one alkoxylated silicone are provided. The silicone portion of the alkoxylated silicone is preferably substituted or unsubstituted dimethicone. Preferably, each alkoxylation group comprises less than 8 carbon atoms, preferably less than 5 carbon atoms, preferably between 2 and 4 carbon atoms, with ethoxylation (2 carbon atoms) and propoxylation (3 carbon atoms) being most preferred. The amount of alkoxylation preferably ranges from 1 to 100, preferably from 2 to 50, preferably from 2 to 30, and preferably from 2 to 20, including all ranges and subranges therebetween. PEG-11 methyl ether dimethicone is especially preferred. According to particularly preferred embodiments, PEG-11 methyl ether dimethicone is combined with PPG-5-buteth-5.

Preferably, the surfactant(s) is/are in the compositions of the present invention in an amount ranging from about 1 to about 30% by weight based on total weight of the composition, preferably about 2% to about 25% by weight based on the total weight of the composition, and preferably about 3% to about 20% by weight based on the total weight of the composition, including all ranges and subranges therebetween.

Hydrophilic Sunscreen Active Agent Comprising a Sulfonic Acid Group

According to the present invention, compositions comprising at least one hydrophilic sunscreen active agent comprising a sulfonic acid group are provided. Acceptable hydrophilic active agents are described, for example, in U.S. Pat. Nos. 6,024,944 and 4,585,597, as well as French patent applications FR 2,236,515, 2,282,426, 2,645,148, 2,430,938 and 2,592,380, the entire contents of all of which are hereby incorporated by reference.

As examples of hydrophilic sunscreen active agents containing at least one $SO_3H$ group, mention may be made more particularly of:
benzene-1,4-[di(3-methylidenecamphor-10-sulphonic acid)];
4-(3-methylidenecamphor)benzenesulphonic acid;
3-benzylidenecamphor-10-sulphonic acid;
2-methyl-5-(3-methylidenecamphor)benzenesulphonic acid;
2-chloro-5-(3-methylidenecamphor)benzenesulphonic acid;
3-(4-methyl)benzylidenecamphor-10-sulphonic acid;
(3-t-butyl-2-hydroxy-5-methyl)benzylidenecamphor-10-sulphonic acid;
(3-t-butyl-2-hydroxy-5-methoxy)benzylidenecamphor-10-sulphonic acid;
(3,5-di-tert-butyl-4-hydroxy)benzylidenecamphor-10-sulphonic acid;
2-methoxy-5-(3-methylidenecamphor)benzenesulphonic acid;
3-(4,5-methylenedioxy)benzylidenecamphor-10-sulphonic acid;
3-(4-methoxy)benzylidenecamphor-10-sulphonic acid;
3-(4,5-dimethoxy)benzylidenecamphor-10-sulphonic acid;
3-(4-n-butoxy)benzylidenecamphor-10-sulphonic acid;
3-(4-n-butoxy-5-methoxy)benzylidenecamphor-10-sulphonic acid; and
2-[4-(camphormethylidene)phenyl]benzimidazole-5-sulphonic acid.

Particularly preferred sunscreen active agents include phenylbenzimidazole sulfonic acid, sulisobenzone, and ecamsule (terephthalylidene dicamphor sulphonic acid [manufactured under the name "Mexoryl SX"]).

Preferably, the at least one hydrophilic sunscreen active agent comprising a sulfonic acid group(s) is/are in the compositions of the present invention in an amount ranging from about 0.5 to about 10% by weight based on total weight of the composition, preferably about 1% to about 9% by weight based on the total weight of the composition, and preferably about 2% to about 8% by weight based on the total weight of the composition, including all ranges and subranges therebetween.

Without wishing to be bound by any particular theory, Applicants believe that when the copolymer of the present invention is combined with the hydrophilic sunscreen active agent comprising a sulfonic acid group in a composition, the copolymer is not able to thicken the composition: the composition breaks down and/or loses viscosity in the presence of the hydrophilic active agent. Also, it is difficult to add coloring agent to such compositions. It was discovered, though, that adding the required surfactants can improve—copolymer/pigment compatibility, and also thicken the composition. However, Applicants also believe that when the copolymer and the required surfactant are present in a composition (without the hydrophilic active agent comprising a sulfonic acid group), the composition pills when applied to the skin. Applicants surprisingly discovered that combining at least one hydrophilic sunscreen active agent comprising a sulfonic acid group, at least one surfactant selected from the group consisting of alkoxylated fatty alcohols, sorbitan esters, alkoxylated silicones, and mixtures thereof, and at least one copolymer comprising a carboxylic acid containing α,β-monoethylenic unsaturation and an ester of a carboxylic acid containing α,β-monoethylenic unsaturation and of an oxyalkylenated fatty alcohol in a composition, a stable, thick, and non-pilling composition can be provided.

Preferably, the surfactant(s) and copolymer(s) comprising a carboxylic acid containing α,β-monoethylenic unsaturation and an ester of a carboxylic acid containing α,β-monoethylenic unsaturation and of an oxyalkylenated fatty alcohol are present in the compositions and methods of the invention in a weight ratio between 3:1 and 1:3, preferably between 2:1 and 1:2, and preferably between 1.5:1 and 1:1.5.

Preferably, the surfactant(s) and the hydrophilic sunscreen active agent comprising a sulfonic acid group are present in the compositions and methods of the invention in a weight ratio between 3:1 and 1:3, preferably between 2:1 and 1:2, and preferably between 1.5:1 and 1:1.5.

Preferably, the hydrophilic sunscreen active agent comprising a sulfonic acid group and copolymer(s) comprising a carboxylic acid containing α,β-monoethylenic unsaturation and an ester of a carboxylic acid containing α,β-monoethylenic unsaturation and of an oxyalkylenated fatty alcohol are present in the compositions and methods of the invention in a weight ratio between 3:1 and 1:3, preferably between 2:1 and 1:2, and preferably between 1.5:1 and 1:1.5.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, additional sunscreen active agents, preserving agents, fragrances, fillers, neutralizing agents, cosmetic and dermatological active agents such as, for example, emollients, moisturizers, vitamins, essential fatty acids, additional surfactants, silicone elastomers, thickening agents, gelling agents, particles, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

With respect to other sunscreen active agents (which do not comprise a sulfonic acid group) which can be added to the compositions of the present invention, mention can be made of organic sunscreens such as anthranilates; cinnamic derivatives; dibenzoylmethane derivatives; salicylic derivatives; camphor derivatives; triazine derivatives, such as those disclosed in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis(hydroxyphenylbenzotriazole) derivatives as disclosed in Applications U.S. Pat. Nos. 5,237,071, 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; 4,4-diarylbutadienes as disclosed in Applications EP 0 967 200, DE 197 46 654, DE 197 55 649, EP-A-1 008 586, EP 1 133 980 and EP 133 981; and their mixtures.

By way of illustration, mention may be made, as sunscreens which are generally active in the UV-A and/or UV-B regions, denoted below under their INCI names, of:

p-aminobenzoic acid (PABA) derivatives, in particular PABA, ethyl PABA, ethyl dihydroxypropyl PABA, ethylhexyl dimethyl PABA, glyceryl PABA or PEG-25 PABA, salicylic derivatives, in particular homosalate, ethylhexyl salicylate, dipropylene glycol salicylate, or TEA salicylate, dibenzoylmethane derivatives, in particular butyl methoxydibenzoylmethane (sold in particular under the trade name "Parsol 1789"), or isopropyl dibenzoylmethane, cinnamic derivatives, in particular ethylhexyl methoxycinnamate (sold in particular under the trade name "Parsol MCX"), isopropyl methoxycinnamate, isoamyl methoxycinnamate, cinoxate, DEA methoxycinnamate, diisopropyl methyl cinnamate, or glyceryl ethylhexanoate dimethoxycinnamate, β,β-diphenylacrylate derivatives, in particular octocrylene (sold in particular under the trade name "Uvinul N539") or etocrylene, benzophenone, in particular benzophenone-1, benzophenone-2, benzophenone-3 or oxybenzone, benzophenone-5, benzophenone-6, benzophenone-8, benzophenone-9, benzophenone-12, or n-hexyl 2-(4-diethylamino-2-hydroxybenzoyl)benzoate, benzylidene camphor derivatives, in particular 3-benzylidene camphor, 4-methylbenzylidene camphor, or polyacrylamidomethyl benzylidene camphor (manufactured under the name "Mexoryl SW"), triazine derivatives, in particular anisotriazine (sold under the trade name "Tinosorb 5"), ethylhexyl triazone, diethylhexyl butamido triazone, or 2,4,6-tris(diisobutyl 4'-aminobenzalmalonate)-s-triazine, benzotriazole derivatives, in particular drometrizole trisiloxane or methylene bisbenzotriazolyl tetramethylbutylphenol, anthranilic derivatives, in particular menthyl anthranilate, imidazoline derivatives, in particular ethylhexyl dimethoxybenzylidene dioxoimidazoline propionate, benzalmalonate derivatives, in particular polyorganosiloxane comprising benzalmalonate functional groups, 4,4-diarylbutadiene derivatives, in particular 1,1'-dicarboxy (2,2'-dimethylpropyl)-4,4-diphenylbutadiene, and their mixtures.

With respect to Inorganic sunscreens that can be added, mention may be made of pigments or alternatively nanopigments (mean size of the primary particles: generally between 5 nm and 100 μn, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments. Conventional coating agents of such inorganic sunscreen active agents include alumina and/or aluminium stearate. Examples of nanopigments formed from coated or uncoated metal oxides are disclosed in particular in Patent Applications EP 518 772 and EP 518 773.

According to preferred embodiments of the present invention, methods of treating, caring for and/or making up keratinous material such as skin and lips by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less.

According to a preferred embodiment of the present invention, compositions having improved cosmetic properties such as, for example, improved stability, feel (reduced tackiness) and/or spreadability (reduced pilling) properties are provided.

According to further embodiments of the present invention, methods of improving the stability, feel (reduced tackiness) and/or spreadability (reduced pilling) of a composition, preferably a makeup compositions such as a foundation or lip composition, comprising adding at least one hydrophilic sunscreen active agent comprising a sulfonic acid group, at least one surfactant selected from the group consisting of alkoxylated fatty alcohols, sorbitan esters, alkoxylated silicones, and mixtures thereof, and at least one copolymer comprising at least one monomer comprising a carboxylic acid containing α,β-unsaturation, at least one monomer containing an ester of a carboxylic acid containing α,β-unsaturation, and at least one monomer containing an oxyalkylenated fatty alcohol to the composition are provided. If pigments are present in the composition, preferably acidic components such as, for example, acidic copolymers (e.g., Aculyn-22) and acidic sunscreen active agents (e.g., phenylbenzimidazole sulfonic acid) are neutralized, either separately or together, with a base compound prior to combination with pigments. Typically, such neutralization occurs by adding a base compound to a phase containing acidic component(s) prior to addition of pigments to the phase.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Composition Preparation

To prepare a composition of the present invention, the copolymer (Aculyn-22), hydrophilic sunscreen active agent (phenylbenzimidazole sulfonic acid), and surfactants (polysorbate-85, sorbitan sesquiolate, and/or PEG-11 methyl ether dimethicone/PPG-5-buteth-5) are combined in a water phase. This phase may also contain a pigment grind that was prepared by combining pigments in water under high shear or other suitable means to wet and grind the pigments. If a pigment grind phase is included, the surfactants are more suitably combined in this phase to aid pigment wetting, rather than combining directly with copolymer and hydrophilic sunscreen agent. The total combined water phase is preferably neutralized using a suitable base to a pH equal or greater than 7.5. Suitable bases may include sodium hydroxide or aminomethyl propanol. If pigments are present in the composition, such neutralization occurs prior to combination with the pigments.

Oils contained within the oil phase, which may comprise a mixture of petroleum-based or silicone-based ingredients, are combined in an oil phase, which is then added to the total water phase at under high shear to form an emulsion.

Powders and fillers can be added to the emulsion after formation. If jet-milled pigments, combined with fillers such as synthetic fluorphlogopite, are used in the formulation, they may be added after the emulsion is formed. The final pH is adjusted again to a pH equal or greater than 7.5 using a suitable base.

EXAMPLE 2

Various combinations of copolymer (Aculyn-22), sunscreen agents, and surfactants were examined in a base composition (foundation) prepared according to the procedures in example 1 (or in a substantially identical base composition differing only in minor ways to account for the different ingredients being added, where the minor differences in base compositions did not affect our experiments). It was determined whether the compositions were stable (if the compositions immediately underwent phase separation or did not form an emulsion, the compositions were deemed to be unstable), thick (defined as having a viscosity greater than or equal to 130 cPs as measured via standard methodology), or pilled upon application.

The base composition is set forth below:

| Phase | Ingredient | Amount |
|---|---|---|
| A | WATER | To 100 |
|  | GLYCERIN | 7.00 |
|  | PROPANEDIOL | 5.00 |
|  | SORBITAN SESQUIOLEATE | Defined in table below |
|  | POLYSORBATE 85 | Defined in table below |
|  | PEG-11 METHYL ETHER DIMETHICONE (and) PPG-5-BUTETH-5 | Defined in table below |
|  | DISODIUM EDTA | 0.20 |
|  | ACRYLATES/STEARETH-20 METHACRYLATE COPOLYMER | Defined in table below |
|  | PHENYLBENZIMIDAZOLE SULFONIC ACID | Defined in table below |
|  | PHENOXYETHANOL | 0.70 |
|  | CAPRYLYL GLYCOL | 0.50 |
|  | AMINOMETHYL PROPANOL | 0.00 |
| B | ETHYLHEXYL METHOXYCINNAMATE | Defined in table below |
| C | HDI/TRIMETHYLOL HEXYLLACTONE CROSSPOLYMER | 1.00 |
| D | PIGMENTS | 11.11 |
|  | TOTAL | 100.00 |

The results are set forth in the table below:

| % of Aculyn-22 | Surfactant (%) | Sunscreens (%) | Unstable? | Thick? | Pill? |
|---|---|---|---|---|---|
| 4.25 | Potassium Cetyl Phosphate (3.0) | N | N | Y | Y |
| 4.25 | N | N | N | Y | Y |
| 4.25 | N | Mexoryl (3) PBSA (3) | Y | — | — |
| 4.25 | N | N | N | Y | Y |
| 4.25 | Trilaureth-4 Phosphate (1.18) | N | Y | Y | Y |
| 4.25 | Abil 85 (1.5) | N | N | Y | Y |
| 2.1 | Abil 85 (1.5) | N | Y | Y | Y |
| 4.25 | N | OMC (7) | N | Y | Y |
| 4.25 | Sorbitan Sesquioleate (0.26) Laureth-4 (0.32) | OMC (7) | N | Y | N |
| 4.25 | N | Mexoryl (3) PBSA (9) | Y | N | — |
| 4.25 | Sorbitan Sesquioleate (1.66) Laureth-4 (2.0) | Mexoryl (3) PBSA (9) | N | Y | N |
| 4.25 | Trilaureth-4 Phosphate (1.0) | Mexoryl (3) PBSA (9) | Y | N | — |
| 4.25 | Sorbitan Sesquioleate (1.8) Laureth-4 (2.2) | Mexoryl (3) PBSA (9) | Y | Y | N |
| 4.25 | Sorbitan Sesquioleate (4.0) | Mexoryl (3) PBSA (9) | Y | N | — |
| 4.25 | Sorbitan Sesquioleate (1.8) Laureth-4 (2.2) | Mexoryl (3) PBSA (9) | N | Y | N |
| 2 | Sorbitan Sesquioleate (0.55) Polysorbate 85 (0.45) | PBSA (3) | Y | Y | N |
| 2 | Sorbitan Sesquioleate (0.55) Polysorbate 85 (0.45) | OMC (7.5) | Y | Y | Y |
| 2 | Sorbitan Sesquioleate (2.75) Polysorbate 85 (2.25) | PBSA (2.7) OMC (6.8) | Y | Y | N |
| 2 | Sorbitan Sesquioleate (1.65) Polysorbate 85 (1.35) PEG-11 Methyl Ether Dimethicone (1.00) | PBSA (2.7) OMC (6.8) | Y | Y | N |
| 4.25 | Sorbitan Sesquioleate (1.65) Polysorbate 85 (1.35) PEG-11 Methyl Ether Dimethicone (1.00) | PBSA (2.7) OMC (6.8) | N | Y | N |
| 4.25 | Sorbitan Sesquioleate (1.65) PEG-11 Methyl Ether Dimethicone (1.00) | PBSA (2.7) OMC (6.8) | N | Y | N |

PBSA = phenylbenzimidazole sulfonic acid
Mexoryl = ecamsule
OMC = octylmethoxycinnamate The results can be summarized as follows: combining the copolymer with the hydrophilic sunscreen agent comprising a sulfonic acid group resulted in a very thin, unstable mixture. Combining the copolymer with surfactants resulted in a very thick, stable composition which pilled upon application. However, compositions of the present invention containing copolymer, the required surfactants and the required sunscreen active agent were thick (having a viscosity greater than or equal to 130 cPs) and stable and did not pill upon application. Further, the invention compositions were stable gel compositions having a nice and cushiony structure. Samples of the compositions placed in a jar after being touched returns to its original flat surface without leaving traces of touching.

EXAMPLE 3

Exemplified Water Gel Foundations of the Present Invention

Composition A

| Phase | Ingredient | % |
|---|---|---|
| A | WATER | 17.0 |
|  | GLYCERIN | 7.00 |
|  | PROPANEDIOL | 5.00 |
|  | SORBITAN SESQUIOLEATE | 1.65 |
|  | POLYSORBATE 85 | 1.35 |
|  | PEG-11 METHYL ETHER DIMETHICONE (and) PPG-5-BUTETH-5 | 1.00 |
|  | TITANIUM DIOXIDE | 5.95 |
|  | IRON OXIDES | 0.63 |
|  | IRON OXIDES | 0.35 |
|  | IRON OXIDES | 0.07 |
| B | WATER | 17.0 |
|  | ACRYLATES/STEARETH- | 2.00 |

| Phase | Ingredient | % |
|---|---|---|
| | 20 METHACRYLATE COPOLYMER | |
| C | WATER | 25.8 |
| | PHENYLBENZIMIDAZOLE SULFONIC ACID | 2.70 |
| D | ETHYLHEXYL METHOXYCINNAMATE | 6.80 |
| | PHENOXYETHANOL | 0.50 |
| | CAPRYLYL GLYCOL | 0.50 |
| E | DIMETHICONE | 2.74 |
| | DIMETHICONE (and) DIMETHICONOL | 0.88 |
| F | HDI/TRIMETHYLOL HEXYLLACTONE CROSSPOLYMER | 1.00 |
| | TOTAL | 100 |

Composition B

| Phase | Ingredient | Amount |
|---|---|---|
| A | WATER | 15.85 |
| | GLYCERIN | 7.00 |
| | PROPANEDIOL | 5.00 |
| | SORBITAN SESQUIOLEATE | 2.20 |
| | POLYSORBATE 85 | 1.80 |
| | TITANIUM DIOXIDE | 5.95 |
| | IRON OXIDES | 0.63 |
| | IRON OXIDES | 0.35 |
| | IRON OXIDES | 0.07 |
| B1 | WATER | 29.50 |
| | PHENYLBENZIMIDAZOLE SULFONIC ACID | 3.00 |
| B2 | WATER | 17.00 |
| | ACRYLATES/STEARETH-20 METHACRYLATE COPOLYMER | 2.00 |
| B3 | AMINOMETHYL PROPANOL | 1.15 |
| C | ETHYLHEXYL METHOXYCINNAMATE | 7.50 |
| D | PHENOXYETHANOL | 0.50 |
| | CAPRYLYL GLYCOL | 0.50 |
| E | AMINOMETHYL PROPANOL | 0.00 |
| | TOTAL | 100.00 |

Composition C

| Phase | Ingredient | Amount |
|---|---|---|
| A | WATER | 20.00 |
| | GLYCERIN | 7.00 |
| | PROPANEDIOL | 5.00 |
| | TRIETHYL CITRATE | 3.50 |
| | ETHYLHEXYLGLYCERIN | 1.00 |
| | SORBITAN SESQUIOLEATE | 1.80 |
| | LAURETH-4 | 2.20 |
| | TITANIUM DIOXIDE | 5.95 |
| | IRON OXIDES | 0.63 |
| | IRON OXIDES | 0.35 |
| | IRON OXIDES | 0.07 |
| B1 | WATER | 19.25 |
| | PHENYLBENZIMIDAZOLE SULFONIC ACID | 3.00 |
| | TEREPHTHALYLIDENE DICAMPHOR SULFONIC ACID | 9.00 |
| B2 | SODIUM HYDROXIDE | 0.00 |
| B3 | WATER | 17.00 |
| | ACRYLATES/STEARETH-20 METHACRYLATE COPOLYMER | 4.25 |
| B4 | SODIUM HYDROXIDE | 0.00 |
| C | SODIUM HYDROXIDE | 0.00 |
| | TOTAL | 100.00 |

What is claimed is:

1. A composition comprising (1) water, (2) at least one hydrophilic sunscreen active agent comprising a sulfonic acid group, (3) at least one surfactant selected from the group consisting of alkoxylated fatty alcohols, sorbitan esters, alkoxylated silicones, and mixtures thereof, (4) at least one copolymer comprising at least one monomer comprising a carboxylic acid containing α, β-unsaturation, at least one monomer containing an ester of a carboxylic acid containing α, β-unsaturation, and at least one monomer containing an oxyalkylenated fatty alcohol, and (5) at least one coloring agent, wherein the surfactant(s) and copolymer(s) are present in a weight ratio between 3:1 and 1:3 and wherein the hydrophilic sunscreen active agent(s) and copolymer(s) are present in a weight ratio between 3:1 and 1:3.

2. The composition of claim 1, wherein the composition is an emulsion.

3. The composition of claim 2, wherein the emulsion is an oil-in-water emulsion.

4. The composition of claim 1, wherein the hydrophilic sunscreen active agent is selected from the group consisting of phenylbenzimidazole sulfonic acid, sulisobenzone, and ecamsule.

5. The composition of claim 4, wherein the copolymer is Acrylates/Steareth-20 Methacrylate Copolymer.

6. The composition of claim 5, wherein the surfactant is selected from the group consisting of sorbitan sesquiolate, polysorbate-85, PEG-11 methyl ether dimethicone, PPG-5-buteth-5, and mixtures thereof.

7. The composition of claim 1, wherein the hydrophilic sunscreen active agent is phenylbenzimidazole sulfonic acid.

8. The composition of claim 7, wherein the copolymer is Acrylates/Steareth-20 Methacrylate Copolymer.

9. The composition of claim 5, wherein the surfactant is selected from the group consisting of sorbitan sesquiolate, polysorbate-85, PEG-11 methyl ether dimethicone, PPG-5-buteth-5, and mixtures thereof.

10. The composition of claim 9, wherein the surfactant(s) and the hydrophilic sunscreen active agent are present in a weight ratio between 3:1 and 1:3.

11. The composition of claim 10, comprising 3% or less oil by weight with respect to the total weight of the composition.

12. The composition of claim 9, comprising 3% or less oil by weight with respect to the total weight of the composition.

13. The composition of claim 1, wherein the copolymer is Acrylates/Steareth-20 Methacrylate Copolymer.

14. The composition of claim 13, wherein the surfactant is selected from the group consisting of sorbitan sesquiolate, polysorbate-85, PEG-11 methyl ether dimethicone, PPG-5-buteth-5, and mixtures thereof.

15. The composition of claim 1, wherein the surfactant is selected from the group consisting of sorbitan sesquiolate, polysorbate-85, PEG-11 methyl ether dimethicone, PPG-5-buteth-5, and mixtures thereof.

16. The composition of claim 1, wherein the surfactant(s) and the hydrophilic sunscreen active agent are present in a weight ratio between 3:1 and 1:3.

17. The composition of claim 1, comprising 3.6% or less oil by weight with respect to the total weight of the composition.

18. The composition of claim 1, comprising 3% or less oil by weight with respect to the total weight of the composition.

19. A method of preparing a composition comprising combining (1) water, (2) at least one hydrophilic sunscreen active agent comprising a sulfonic acid group, (3) at least one surfactant selected from the group consisting of sorbitan esters, alkoxylated silicones, and mixtures thereof, (4) at least one copolymer comprising at least one monomer comprising a carboxylic acid containing $\alpha,\beta$-unsaturation, at least one monomer containing an ester of a carboxylic acid containing $\alpha,\beta$-unsaturation, and at least one monomer containing an oxyalkylenated fatty alcohol to form a composition, and (5) at least one coloring agent, wherein the surfactant(s) and copolymer(s) are combined in a weight ratio between 3:1 and 1:3 and wherein the hydrophilic sunscreen active agent(s) and copolymer(s) are combined in a weight ratio between 3:1 and 1:3.

\* \* \* \* \*